(12) United States Patent
Tutuncu et al.

(10) Patent No.: US 7,040,169 B2
(45) Date of Patent: May 9, 2006

(54) USE OF CUTTINGS FOR REAL TIME ATTENUATION PREDICTION

(75) Inventors: Azra Nur Tutuncu, Houston, TX (US); Michael Tolbert Myers, Sugar Land, TX (US); Mohammad Michael Arasteh, Houston, TX (US)

(73) Assignee: Shell Oil Company, Houston, TX (US)

( * ) Notice: Subject to any disclaimer, the term of this patent is extended or adjusted under 35 U.S.C. 154(b) by 96 days.

(21) Appl. No.: 10/493,366

(22) PCT Filed: Oct. 24, 2002

(86) PCT No.: PCT/US02/34385

§ 371 (c)(1),
(2), (4) Date: Apr. 23, 2004

(87) PCT Pub. No.: WO03/036288

PCT Pub. Date: May 1, 2003

(65) Prior Publication Data

US 2005/0016280 A1 Jan. 27, 2005

Related U.S. Application Data

(60) Provisional application No. 60/336,413, filed on Oct. 24, 2001.

(51) Int. Cl.
*G01N 29/032* (2006.01)
*G01V 1/40* (2006.01)
(52) U.S. Cl. .......................... 73/602; 73/152.05; 702/11
(58) Field of Classification Search ................ 73/602, 73/152.03, 152.04, 152.11, 599; 181/108, 181/122; 702/6, 11
See application file for complete search history.

(56) References Cited

U.S. PATENT DOCUMENTS

| | | | |
|---|---|---|---|
| 2,735,503 A * | 2/1956 | Rice et al. .................. 181/122 |
| 3,135,685 A * | 6/1964 | Tanner et al. ............... 209/269 |
| 4,380,930 A | 4/1983 | Podhrasky et al. ........... 73/594 |
| 4,577,503 A | 3/1986 | Imaino et al. ................ 73/602 |
| 4,598,392 A | 7/1986 | Pann ........................... 367/32 |
| 4,631,963 A | 12/1986 | Sprunt et al. ................. 73/594 |
| 5,305,239 A * | 4/1994 | Kinra .......................... 702/39 |
| 6,481,289 B1 * | 11/2002 | Dixon et al. .................. 73/602 |
| 6,769,307 B1 * | 8/2004 | Dixon et al. .................. 73/602 |
| 6,968,274 B1 * | 11/2005 | Tutuncu et al. ............... 702/11 |
| 2004/0236513 A1 * | 11/2004 | Tutuncu et al. ............... 702/11 |
| 2005/0197780 A1 * | 9/2005 | Moos et al. .................. 702/14 |

OTHER PUBLICATIONS

Rig-site and laboratory use of CWT acoustic velocity measurements on cuttings, by NES, et al, Society of Petroleum Engineers, paper No. 36854.

The influence of fluids on grain contact stiffness and frame moduli in sedimentary rocks by Tutuncu, A., et al. Geophysics, vol. 57, No. 12 Dec. 1992, pp. 1571-1582.

(Continued)

*Primary Examiner*—Hezron Williams
*Assistant Examiner*—Jacques Saint-Surin (57) ABSTRACT

A method is disclosed for predicting attenuation in real time while drilling using a portable continuous wave technology (CWT) tool to obtain amplitude spectra as a function of frequency for the cuttings at the rig site. Attenuation is predicted, and plotted as a function of frequency to monitor hydrocarbon content changes, fluid front moves, and pressure mapping or plotting attenuation as a function of depth to calibrate high resolution seismic data and interpret amplitudes for formation permeability determination.

16 Claims, 6 Drawing Sheets

Experimental Set-up

OTHER PUBLICATIONS

Y. Mezon, "Physical Acoustics under Reduction", Saveijev I. V. "Cource of General Physics", Nauka, M. 1978, pp. 256-257.

Javorsky, B. M., et al., "Physics Reference Book", bu. Nauka. M. 1965, pp. 452-453.

Letter from Gorodissky & Partners containing a translation of a Office Action issued by the Euration Patent Organization and comments in English on documents AT and AU.

* cited by examiner

Figure 1: Experimental Set-up

Figure 2: CWT resonance spectrum for a 2.5 mm thick shale cutting

Figure 3: Schematic definition of attenuation calculation from CWT amplitude spectra.

Figure 4: CWT velocity as a function of frequency for reference materials Lucite® and salt.

Figure 5: CWT attenuation as a function of frequency for reference materials Lucite® and salt.

Figure 6: Wave velocity as a function of frequency modeled in Tutuncu et al (1992).

Figure 7: Wave attenuation as a function of frequency modeled in Tutuncu et al (1992).

Figure 8: CWT velocity as a function of frequency for water sample.

Figure 9: CWT velocity modeling from dry velocity using Gassmann equation.

Figure 10: CWT attenuation collected in real time in a Gulf of Mexico well.

Figure 11: Use of CWT attenuation for permeability determination in real time in a Gulf of Mexico well.

USE OF CUTTINGS FOR REAL TIME ATTENUATION PREDICTION

This application claims the benefit of Provisional Application No. 60/336,413, filed Oct. 24, 2001.

FIELD OF THE INVENTION

This invention generally relates to the analysis and interpretation of wave attenuation and velocity in cutting samples obtained while drilling. More particularly, this invention relates to amplitude spectra provided by a portable continuous wave technique (Hereafter CWT) tool that measures cuttings at high resonant frequency and to analysis of the amplitude spectra by methodology developed by the inventors to provide a prediction of attenuation in real time at the rig site. The method provides accurate attenuation measurements that offer small error margin that is not otherwise obtainable in the art using seismic, vertical seismic profiling (VSP), or check shot velocities in the field in real time.

BACKGROUND OF THE INVENTION

Attenuation is an inelastic process that dissipates energy by conversion of acoustic energy into heat, thus decreasing wave amplitude and modifying the frequency and phase content of a propagating wavelet. Most of the measurements, processing, and interpretation efforts in the industry and in academia have concentrated on wave velocity rather than attenuation data since velocity measurements are easier to conduct, more reliable and efficient. There is a growing interest recently in attenuation measurements. The frequency content, phase spectrum, and velocity can be used as strong indicators of the type of pore fluid in a formation. Presently in the art, attenuation could only be determined using core samples and it would be impossible to obtain such calculations in real time while drilling.

Ultrasonic attenuation measurements using core samples are known. For example, U.S. Pat. No. 4,380,930 discloses a system for transmitting ultrasonic energy through a material sample which includes an ultrasonic energy transducing means in contact with said material sample for transmitting ultrasonic energy into said sample and for receiving the energy after it has traveled through said sample, a pressure cell for housing said sample under a confining pressure simulating subterranean pressure conditions, and means for isolating said ultrasonic energy transducing means from the confining pressure conditions on said cell such that said ultrasonic energy transducing means operates at ambient pressure conditions.

U.S. Pat. No. 4,631,963 discloses a method for measuring acoustic energy anisotropy of a core sample from a subterranean formation wherein the sample is shaped to provide a plurality of pairs of parallel, planar outer surfaces about the length of the core sample, and acoustic travel time, attenuation, waveform or other acoustic properties are measured through said core sample in each of the azimuthal directions through said core sample which are perpendicular to each of said pairs of parallel, planar outer surfaces, and each of said measured acoustic properties are compared to identify the azimuthal direction of any acoustic energy anisotropy through said core sample. Also see U.S. Pat. No. 4,631,964.

Cuttings produced during drilling represent a potential quasi-real time source of information that can be procured at the rig site. The use of cuttings has been limited in the past, partly due to the difficulties in performing measurements on very small samples and obtaining any kind of accurate results. Drill cuttings could potentially provide an invaluable source of information for calibrating seismic velocities, logging while drilling (LWD) and/or wireline sonic measurements.

Continuous Wave Technique (Hereafter CWT) has been used in the past for measurement of acoustic phase velocities using core samples. This methodology has been recently utilized in a tool, CWT equipment, that is particularly well suited for testing of small samples like drill cuttings, and measurements on sub-inch shale cuttings.

In "Rig-site and Laboratory use of CWT Acoustic Velocity Measurements on Cuttings", by Nes, et al, Society of Petroleum Engineers Paper No. 36854, 1996, incorporated by reference herein in the entirety, there is presented the use of continuous wave technology (CWT) for measurement of acoustic phase velocities on cuttings using potentially portable equipment that is suitable for testing of small samples of cuttings, thus offering a new source of data that can be attained in quasi real-time at the rig site.

There is a great need in the art for a method that would make it possible to accurately predict velocity and attenuation in real time measurements at the rig, site in various lithologies including shales. If such data were available it would permit calibration of seismic velocities and sonic log velocities and improve our fluid and pressure monitoring capabilities in real time, resulting in significant savings during drilling and production, and would also enhance our reserve estimates.

SUMMARY OF THE INVENTION

In accordance with the foregoing the present invention is a method for the prediction of attenuation in real time, at the rig site, as set out in claim 1. The method uses high resonant frequency continuous waveform (CWT) technology to obtain amplitude spectra as a function of frequency for cuttings in real time and using the data in combination with the method disclosed in the present invention to accurately predict attenuation.

The method for prediction of attenuation in real time at the rig site may comprise:

1. Collecting drill cuttings from selected intervals while drilling;

2. Using a portable continuous wave technology (CWT) tool to obtain amplitude spectra as a function of frequency by:

a) Preparing a sample cutting with two opposite, parallel surfaces separated by a distance L (Length of the sample);

b) Placing sample between P- or S- wave transducers;

c) Sweeping a sinusoidal signal continuously through a proper frequency range;

d) Extracting and registering the envelope of the received amplitude modulated signal; and 3. Determining velocity $V_p$ by measuring $\Delta f$, the linewidth at the halfpower point, for each amplitude peak, and inserting the number into the equation $V_p = 2 L \Delta f$;

4. Determining attenuation by:

a) Identifying $(f_{central})_i$ the maximum height of each amplitude peak i;

b) Measuring $(\Delta f_i)_{@(maxamp/2)}$ the width at half the peak amplitude divided by 2;

c) Determining Quality Factor $Q_i$ at ith peak frequency using the equation:

$$Q_i = \frac{(f_{peak})_i}{(\Delta f)_{i \ @ \ halfpeak}}; \text{ and}$$

d) Predicting attenuation as the inverse of $Q_i$:

$$\text{Attenuation} = \frac{1}{Q_i}.$$

The combination of velocity and attenuation data is significant in any modeling effort for a better understanding of the dispersion (frequency dependent) and fluid saturation effects. The data afforded by the method of the present invention will make it possible to improve information on fluid content of reservoirs using seismic calibrated with velocity-attenuation data.

DETAILED DESCRIPTION OF THE INVENTION

The novel method of the present invention offers a number of advantages over anything currently available in the art. First of all, it offers accurate real time measurement of wave velocity and attenuation using real formation sample measurements at the rig site. It can also provide a prediction of formation porosity and permeability in wells in real time. In today's industry, there is no permeability log present that is recorded in the well. The method of this invention will provide a practical way to gain information about petrophysical properties such as permeability and porosity via attenuation and velocity measurements. The combined wave velocity and attenuation provide reliable determinations of petrophysical properties and a practical and cost efficient source for monitoring fluid content changes in producing fields, as well as during drilling. The monitoring aspect provides significant savings in well design, and optimization of production parameters and reservoir simulation studies. In seismic studies, particularly in 4D seismic interpretations, conversion of qualitative amplitude changes into quantitative saturation and/or pressure maps for reservoir simulator updates is needed. Knowledge of combined attenuation and velocity in real time using the method described in this invention will not only help 4D seismic interpretations, but will assist in seismic analysis differentiating oil from gas, especially when oil reservoir pressure is below bubble point pressure. Real time mapping of fluid and pressure fronts leads to increase in ultimate hydrocarbon recovery and reduction in infill drilling and production cost.

Figure 1:
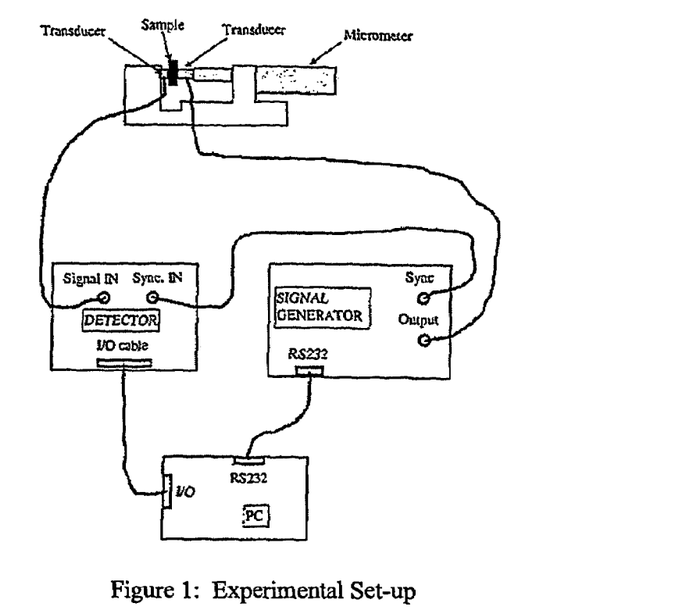
FIG. 1 shows the experimental set-up.
Figure 2:
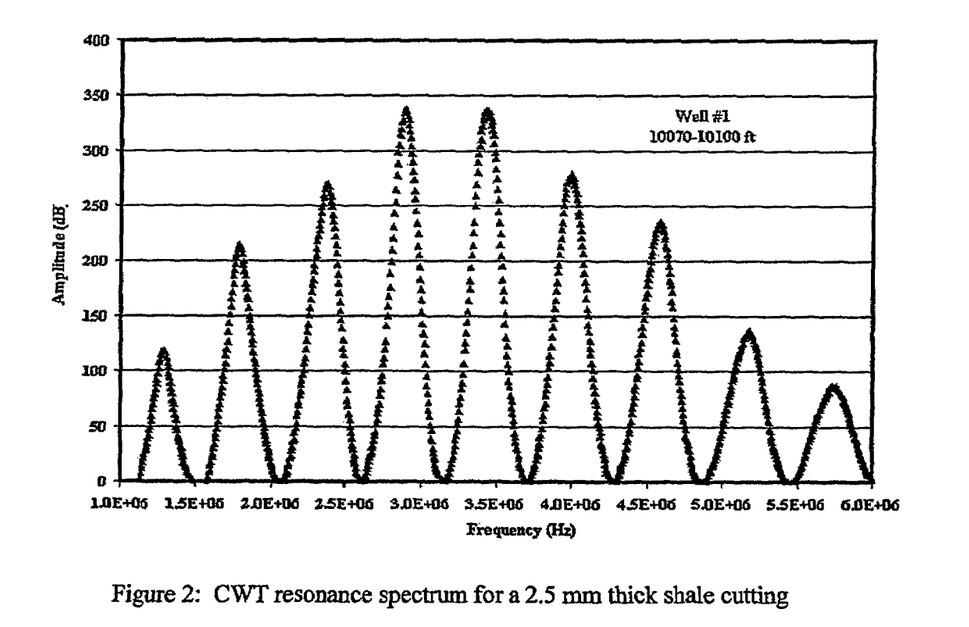
FIG. 2 is a graph of the CWT resonance spectrum for a 2.5-mm thick shale cutting.

The following nomenclature is defined for reference in the description of the invention:
α=acoustic attenuation, Nepers/cm
CW=continuous wave
CWT=continuous wave technique
f=frequency, Hz, $s^{-1}$
D=diameter, m
L, z=sample thickness, m
λ=wavelength, m
mMD RT=measured depth rotary table, m
mTVD=true vertical depth, m
n=number of half-wavelengths, integer
v=velocity of sound, m/s, μs/ft
P=primary wave
ppb=pound per barrel
Q=quality factor
$Q^{-1}$=internal friction
S=shear/secondary wave Subscripts:
n=number of half-wavelengths
p=primary The CWT instrument employed in the present invention to measure small samples of drill cuttings at the rig site is a portable apparatus consisting of a sample holder with two piezoelectric ultrasonic transducers positioned face-to-face. One transducer is used for acoustic wave generation, and the second transducer is used for detection. One of the transducers is mounted on the head of a micrometer that allows simultaneous measurement of the sample length. See FIG. 1. The sample is located between the two transducers. Ultrasonic, standing wave resonances are established in the composite resonator by sweeping the excitation frequency over a range corresponding to several standing wave resonances. A broadband detector with controllable gain that is connected to a laptop PC amplifies the envelope of the received signal. A computer program calculates velocities when several input parameters are provided. An example of the measurement performed on a 2.5-mm thick (0.5 in) shale cutting sample is shown in FIG. 2. The portable CWT apparatus used in the present invention is available commercially from TEMCO Company in Tulsa, Okla.

Figure 3:
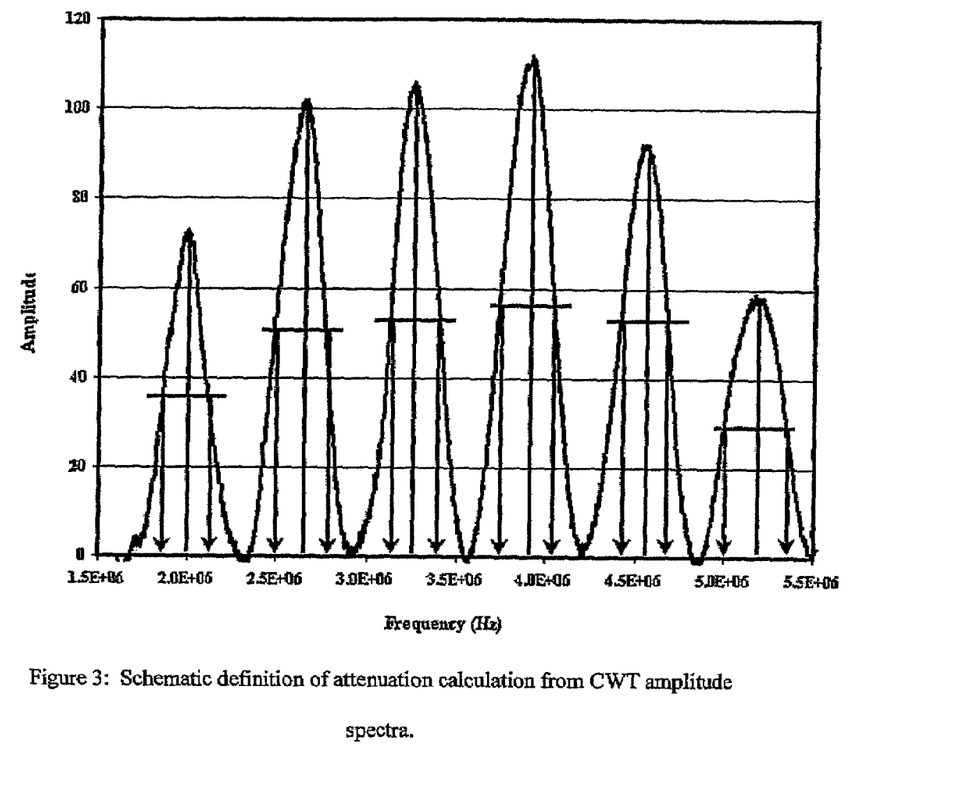
FIG. 3 is a schematic definition of attenuation calculation from CWT amplitude spectra.

The CWT apparatus relies on establishing ultrasonic, standing wave resonances in the composite resonator by sweeping the excitation frequency f over a range corresponding to several standing wave resonances. The resonances are then contained in the amplitude-modulated signal received with the second transducer. Each of the standing wave resonances, n, is characterized by a resonant frequency $f_n$ and a quality factor $Q \equiv f_n/\Delta f_n$ where $\Delta f_n$ is half-width of the peak amplitude (FIG. 3). Frequently, $Q^{-1}$ is denoted as "internal friction", and in case of plane waves related to the acoustic attenuation a as $Q^{-1} = v \cdot \alpha/(\pi \cdot f_n)$. Plane waves are generally assumed here, in practice meaning that λ/D is sufficiently small, where λ is the acoustic wavelength and D the diameter. Resonance will occur essentially each time λ=v/f fulfills L=n·λ/2, where L is the sample thickness, i.e. the distance between the two transducer faces, and n is an integer. The acoustic phase velocity, whether P- or S-wave, can now be expressed as $V_p=2L\Delta f$. Here, $\Delta f \equiv f_{n+1}-f_n$ is the difference in frequency between two consecutive resonances. For example, a shale with $V_p$ of 6550 ft/s and L=0.06 inch would display $\Delta f \approx 0.67$ MHz, and the practical frequency would be in the range of 1–10 MHz.

In preparation for obtaining a measurement the operator prepares a sample drill cutting with two opposite, parallel surfaces separated by a distance L (Length of the sample). Preparation of the sample comprises obtaining two smooth and parallel surfaces and can be accomplished using abrasive sandpaper. The selection of drill cuttings must be done carefully to reduce possible errors from depth uncertainties, heterogeneities, and mechanical damage of cuttings and/or cavings. It is possible to prepare and measure samples, including finely grained samples with thicknesses in fraction of inches in approximately less than 10 minutes after the cutting is captured at the shale shaker.

The sample is clamped between the two transducers while measurements are conducted. The operator attaches P- or S-wave transducers to each of the two surfaces, sweeps a sinusoidal signal continuously through a proper frequency range, extracts and registers the envelope of the received amplitude modulated signal, measures $\Delta f$, and inserts the number into the equation $V_p=2L\Delta f$ to determine velocity.

A micrometer is attached to the metal frame and is used to position the transducer, thus permitting the length of the sample to be measured under the load of the measurement. In order to assure sufficient signal quality without affecting sample properties, a properly selected acoustic coupling gel is used on both prepared sample surfaces.

The method of the present invention provides accurate real time data from sub-inch samples. However, it was observed that, although there were not significant variations in accuracy, samples of 2.5 mm to about 3 mm afforded the most accurate data. Samples smaller than 2.5 mm or samples that were quite thick sometimes resulted in misleading results.

Attenuation is generally more difficult to analyze than other petrophysical properties. In the method of the present invention for predicting attenuation, the frequency is plotted as a function of amplitude, as shown in FIG. 3. A value is determined for $(f_{peak})_i$, the maximum amplitude at the center of each peak i. Then $(\Delta f_i)_{@(halfpeak)}$ is determined by taking the width $\Delta f$ at half of the maximum amplitude at each peak and dividing by 2. These values are then employed to determine $Q_i$, Quality Factor or Internal Friction, using the equation:

$$Q_i = \frac{(f_{peak})_i}{(\Delta f)_{i\ @\ halfpeak}}; \text{ and}$$

Attenuation is predicted as the inverse of $Q_i$:

$$\text{Attenuation} = \frac{1}{Q_i}.$$

Figure 10:
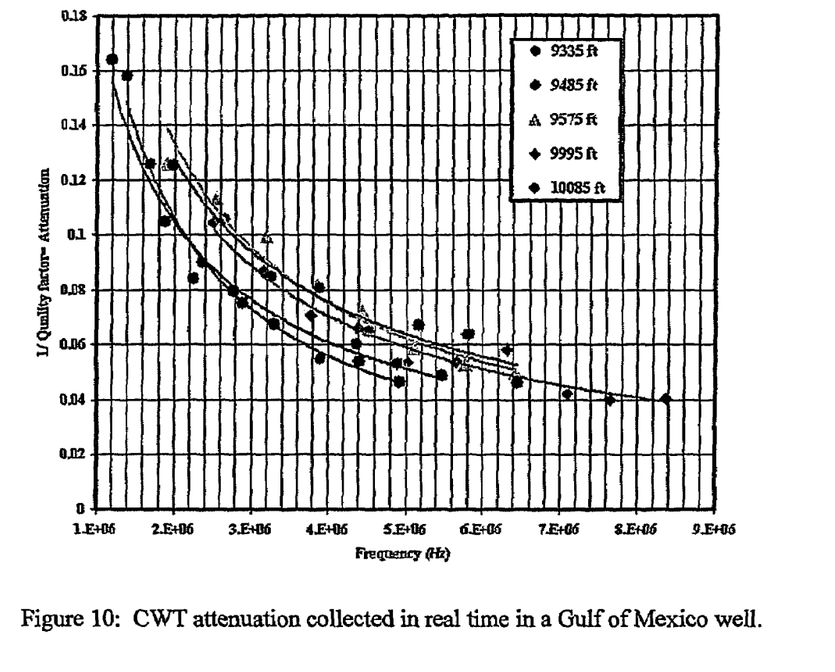
FIG. 10 shows CWT attenuation data collected in real time in a Gulf of Mexico well.

The same calculation is performed for each resonance (peak) amplitude and a value for attenuation is assigned to each resonance frequency. Then the attenuation can be plotted as a function of frequency for monitoring hydrocarbon content changes, fluid front moves and pressure mapping as discussed in Example IV and shown in FIG. 10.

Figure 11:
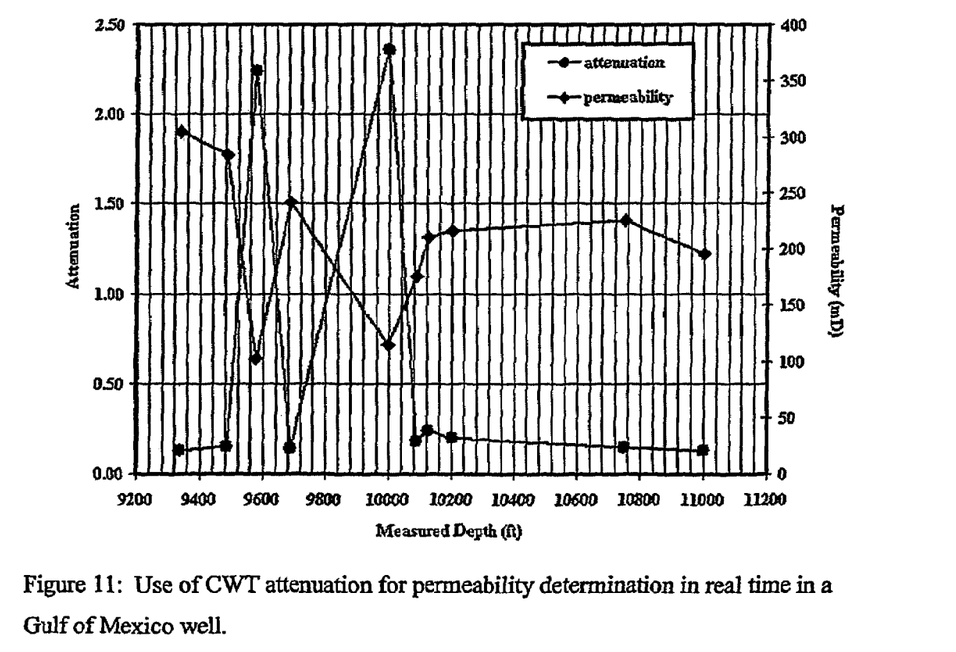
FIG. 11 shows the use of CWT attenuation for permeability determination in real time in a Gulf of Mexico well.

Attenuation can be plotted as a function of depth to, for example, calibrate high resolution seismic data and interpret amplitudes for formation permeability determination, as discussed in Example IV and shown in FIG. 11.

Velocity and attenuation are calculated by proprietary software when several input parameters are provided.

In the present invention we have combined the CWT method for measuring velocities with a new method we have discovered for obtaining accurate measurement of attenuation in preferably fluid saturated samples. The method of the present invention can be utilized for revising interpretation of seismic amplitudes in 3-D and 4-D seismic studies in exploration areas, for lithology descriptions and accurate determination of reserves, and for monitoring fluid and pressure fronts in any producing field. The present invention will also potentially have a powerful impact on deepwater drilling operations due to the fact that combined attenuation and velocity measurements will provide information regarding shallow water flows, abnormal pressure zones, and weak zones that are significantly hazardous in deepwater operations.

The method of the present invention, incorporating the CWT tool, is portable, relatively inexpensive, and easy to operate. Using equipment that can be carried in a briefcase to the rig, velocities can be obtained within minutes and amplitude information can be converted to values for the prediction of attenuation using sub-inch scale samples.

Our experience in an exploration well in real time rig operation with the CWT tool indicated significant deviation from seismic interval velocities, however there was much better agreement with wireline sonic when at a later stage wireline sonic data was collected. Attenuation data was found very reliable when samples were appropriately selected and carefully prepared.

The following examples will serve to illustrate the invention disclosed herein. The examples are intended only as a means of illustration and should not be construed as limiting the scope of the invention in any way. Those skilled in the art will recognize many variations that may be made without departing from the spirit of the disclosed invention.

EXPERIMENTAL

Example I

Figure 4:
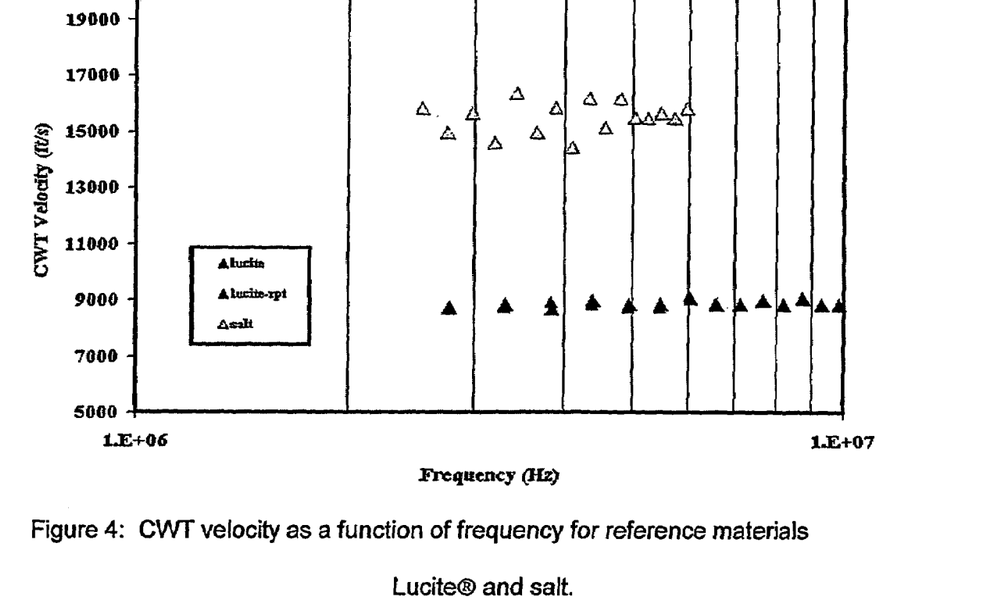
FIG. 4 shows CWT velocity as a function of frequency for reference materials Lucite® and salt.
Figure 5:
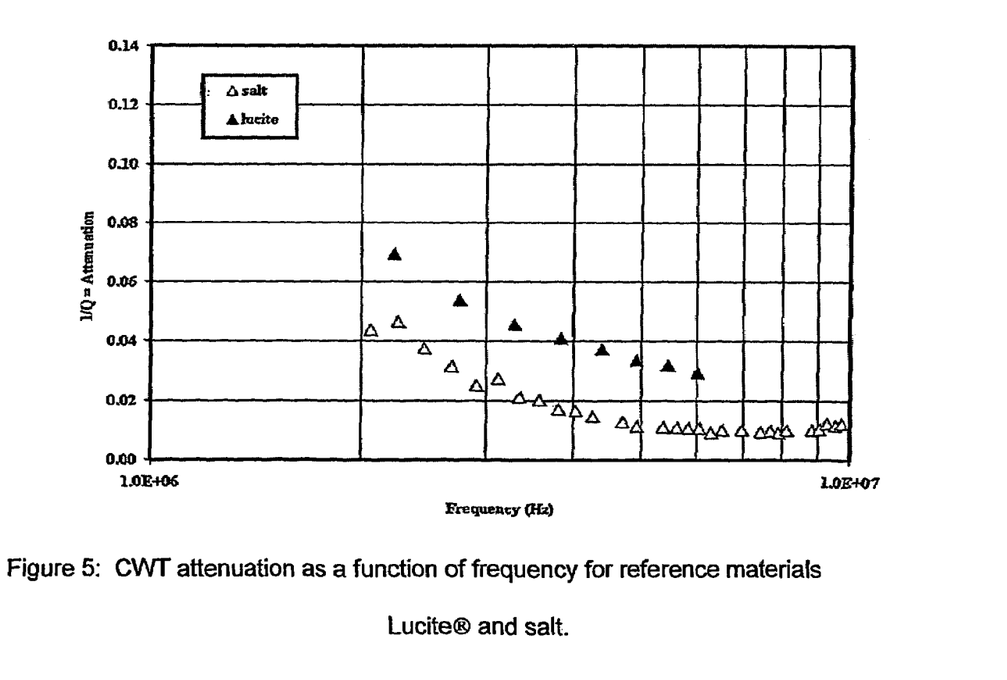
FIG. 5 shows CWT attenuation as a function of frequency for reference materials Lucite® and salt.
Figure 6:
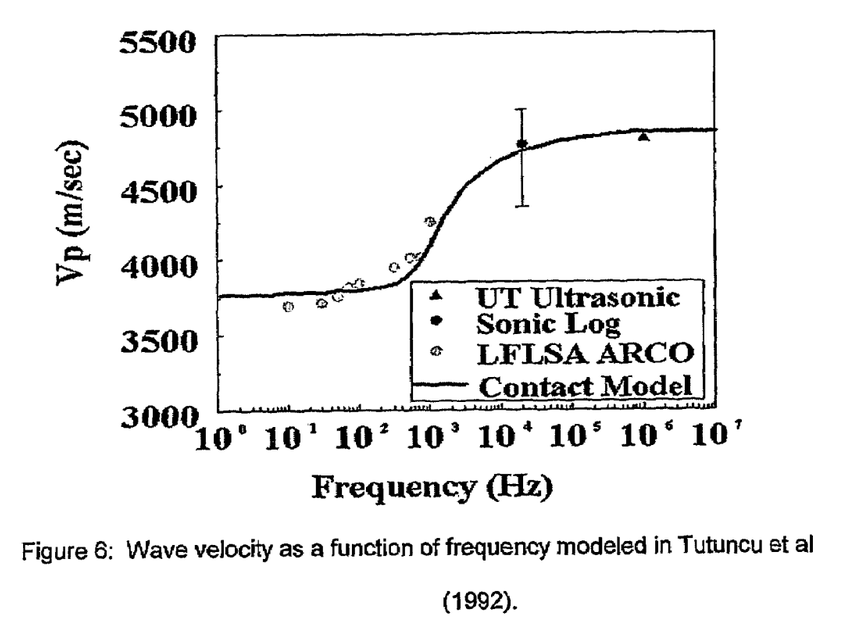
FIG. 6 shows wave velocity as a function of frequency modeled in Tutuncu et al (1992).
Figure 7:
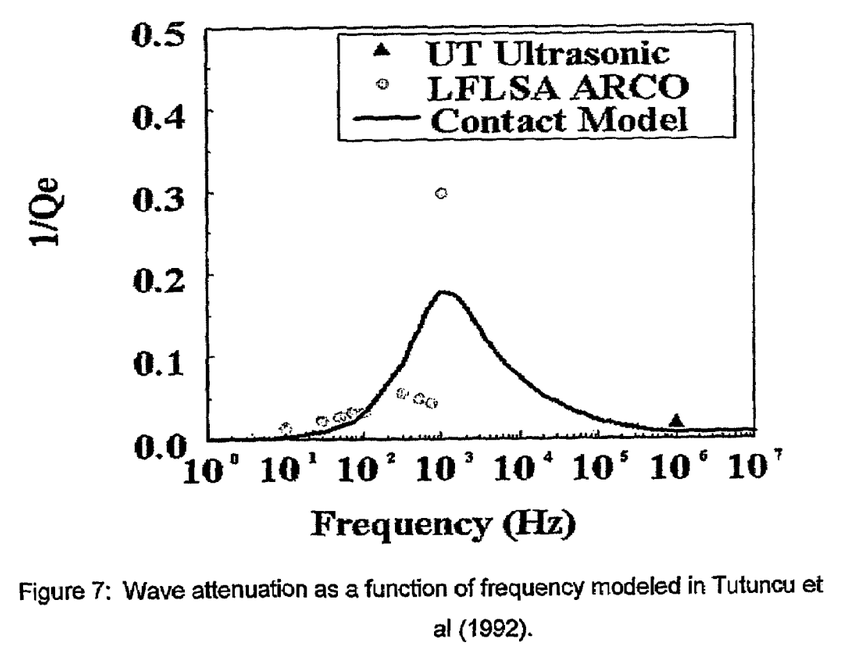
FIG. 7 shows wave attenuation as a function of frequency modeled in Tutuncu et al (1992).

Reference materials were tested in the laboratory and at the rig site to verify the accuracy of the velocity measurement methodology (CWT) that is the source of the input data for the methodology discussed in this invention. Results of the reference velocity and attenuation experiments using Lucite® and salt samples are shown in FIGS. 4 and 5. The salt sample has impurity. This impurity is clearly evident both in the CWT velocity and attenuation spectra as two individual velocity and attenuation profiles, particularly in the lower frequency end of the spectrum. The frequency dependence has been modeled in an article titled "The Influence of Fluids on Grain Contact Stiffness and Frame Moduli in Sedimentary Rocks", by Tutuncu, A., et al., GEOPHYSICS, VOL. 57, NO. 12 (December 1992), pp. 1571–1582, incorporated by reference herein in the entirety. An example of how the model predicts frequency dependence of velocity and attenuation is shown in FIGS. 6 and 7. It is observed that the data obtained by the method of the present invention (for example FIGS. 4 and 5) fits well into the theoretical model. Experiments in frequency range of the measurements obtained with the present invention measure within $10^6$ to $10^7$ Hertz.

Example II

Figure 8:
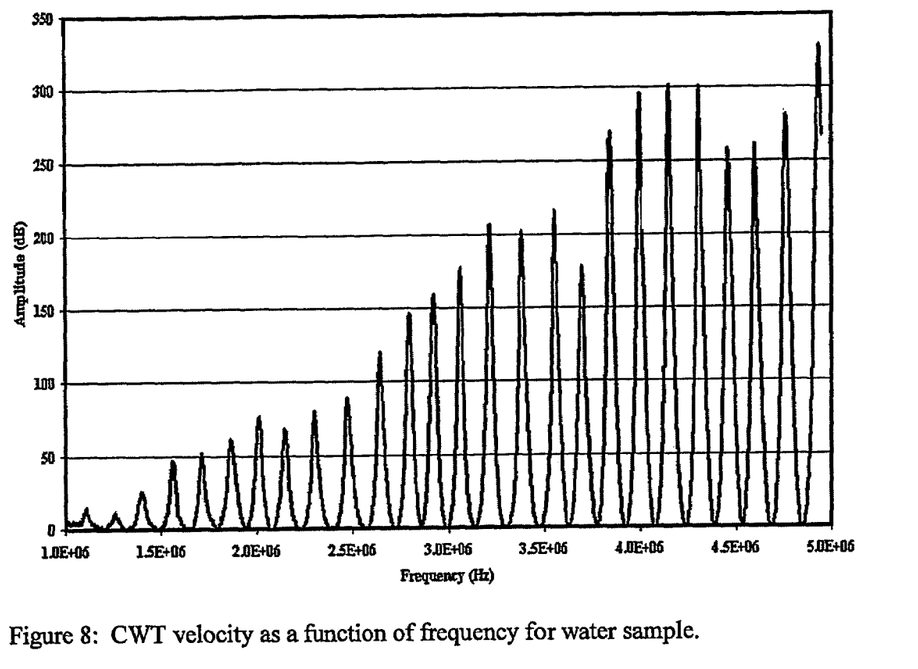
FIG. 8 shows CWT velocity as a function of frequency for a water sample.

In order to account for the fluid type and volume changes, as described in this invention, fluid phase velocity and attenuation was also measured at each test using the CWT apparatus. An example of water CWT amplitude spectra is shown in FIG. 8. The CWT velocity for water was calculated to be 5500±50 ft/s.

Example III

In order to test the accuracy of the method used in monitoring fluid content, several cutting samples were measured dry and then in fully saturated form. Later, a comparison was made using Gassmann fluid substitution to check whether the saturated velocities measured are reliable.

Gassmann's fluid substitution is well-known methodology to predict saturated velocities from dry moduli in low frequency. In this methodology, it is assumed that mineral modulus is homogeneous and pore space is isotropic without any restriction on pore geometry. When a rock is loaded under compression, such as passing seismic wave, an increment of pore pressure change is induced that resists the compression. Therefore, stiffening takes place n rock. Gassmann theory predicts that resulting increase in effective bulk modulus of the saturated rock can be calculated using the following expression:

$$\frac{K_{sat}}{K_g - K_{sat}} = \frac{K_{dry}}{K_g - K_{dry}} + \frac{K_f}{\phi(K_g - K_f)}$$

$$\text{and } \mu_{sat} = \mu_{dry}$$

where $\phi$ is porosity, $K_{sat}$, $K_g$ and $K_f$ are saturated, grain and fluid bulk moduli, respectively. $\mu_{sat}$ and $\mu_{dry}$ are saturated and dry shear modulus for rock. One must be cautious that dry rock is not the same as gas saturated rock.

Figure 9:
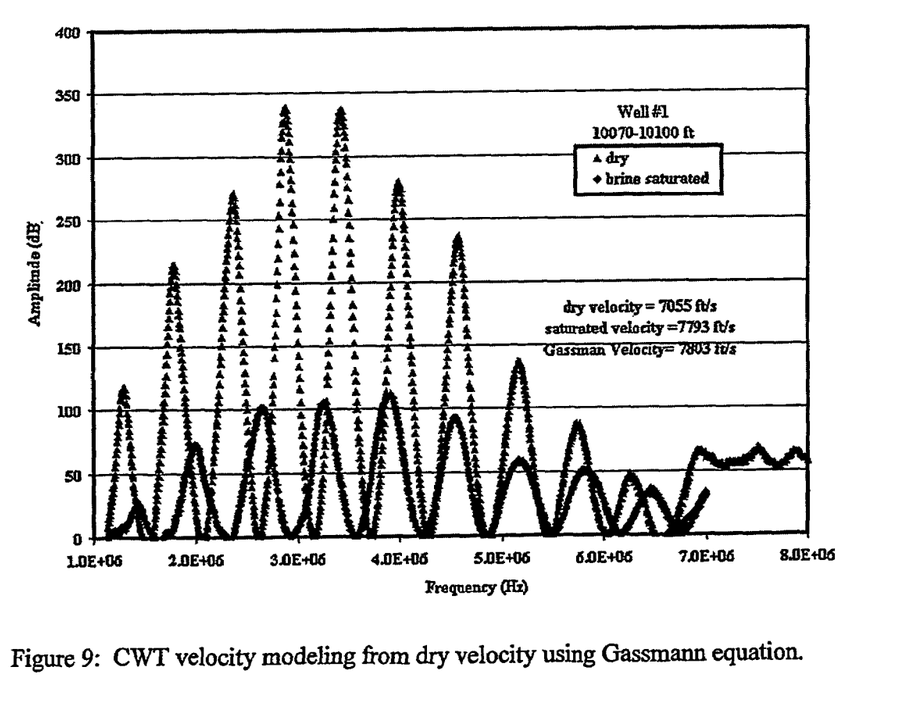
FIG. 9 shows CWT velocity modeling from dry velocity using the Gassmann equation.

The result of our dry and saturated wave amplitude spectra for a Gulf of Mexico drill cutting sample is shown in FIG. 9. As expected, resonance frequencies indicated significant shift when samples were saturated with brine. The observed $\Delta f$, the frequency difference between two consecutive resonances, was small, representing faster velocities due the relationship used calculating CWT velocities ($V_p = 2L\Delta f$). In the example shown in FIG. 9, dry $V_p$ was 7055 ft/s while saturated $V_p$ was 7793 ft/s. When brine was used to predict saturated velocity with Gassmann fluid substitution, the calculated velocity was obtained as 7803 ft/s, less than 0.2% error (0.13%) from the measured values in the laboratory.

Example IV

Several real time attenuation measurement trials were made at a selected interval of a Gulf of Mexico well. CWT Velocity and attenuation data were collected as a well was drilled. Attenuation as a function of frequency for several samples from a well is presented in FIG. 10. It is evident from the data that attenuation is a strong function of frequency. We have used this dependence as a tool for monitoring hydrocarbon content changes, fluid front moves, and pressure mapping. Using high frequency CWT velocity and attenuation measurements, we were able to calibrate high resolution seismic data and interpret amplitudes for formation permeability determination. An example from one of these field trials is presented in FIG. 11.

We claim:

1. A method for predicting attenuation in real time, at the rig site, using a portable continuous wave technology (CWT) tool, which method comprises:
   a) Collecting cuttings at selected intervals while drilling;
   b) Using the CWT tool to obtain amplitude spectra as a function of frequency for each cutting;
   c) Identifying $(f_{peak})_i$ the maximum height of each amplitude peak i;
   d) Measuring $(\Delta f_i)_{@(halfpeak)}$, the width at half of each amplitude peak divided by 2;
   e) Determining Quality Factor $Q_i$, using the equation:

$$Q_i = \frac{(f_{peak})_i}{(\Delta f)_{i\ @\ halfpeak}}; \text{ and}$$

f) Predicting attenuation as the inverse of $Q_i$ $$\text{Attenuation} = \frac{1}{Q_i}.$$

2. The method of claim 1 further comprising plotting attenuation as a function of frequency.
3. The method of claim 2 further comprising using the data in the monitoring of hydrocarbon content changes.
4. The method of claim 2 further comprising using the data in monitoring fluid front moves.
5. The method of claim 2 further comprising using the data in pressure mapping.
6. The method of claim 1 further comprising plotting attenuation as a function depth for an attenuation log.
7. The method of claim 6 further comprising using the data in the calibration of high-resolution seismic data.
8. The method of claim 6 further comprising using the data to interpret amplitudes for formation permeability determination (permeability log).
9. The method of claim 1 further comprising the continuous wave technology (CWT) tool comprises a portable apparatus consisting of a sample holder with two piezoelectric ultrasonic transducers positioned face to face, wherein one transducer is used for acoustic wave generation and a second transducer is used for detection.
10. The method of claim 9 further comprising:
    a) Preparing the cuttings to be placed in the sample holder with two opposite, parallel surfaces separated by a distance L (L =length of the sample cutting);
    b) Placing sample between P- or S- wave transducers;
    c) Sweeping a sinusoidal signal continuously through a proper frequency range; and
    d) Extracting and registering the envelope of the received amplitude modulated signal.
11. The method of claim 1 further comprising the cuttings are collected at intervals that provide accuracy of 5 to 50 ft.
12. The method of claim 11 wherein the cuttings are collected at intervals that provide accuracy of 30 ft.
13. The method of claim 10 wherein the length of the sample L is between about 1.5 and 4mm.
14. The method of claim 1 wherein the cuttings are saturated.
15. The method of claim 1 further comprising the cuttings are selected from shale or other lithologies.
16. The method of claim 1 further comprising the calculations are incorporated into a software program.

* * * * *